United States Patent [19]

Sakamoto et al.

[11] 4,455,310

[45] Jun. 19, 1984

[54] QUINOLINECARBOXYLIC ACID DERIVATIVE, AND ANTIBACTERIAL AGENT CONTAINING SAID COMPOUND AS ACTIVE INGREDIENT

[75] Inventors: Fumio Sakamoto, Osaka; Shoji Ikeda, Ibaraki; Goro Tsukamoto, Toyonaka, all of Japan

[73] Assignee: Kanebo Ltd., Tokyo, Japan

[21] Appl. No.: 382,353

[22] Filed: May 26, 1982

[30] Foreign Application Priority Data

Jun. 10, 1981 [JP] Japan .................................. 56-88061

[51] Int. Cl.³ .................. A61K 31/495; C07D 403/14
[52] U.S. Cl. .................................... 424/250; 544/363
[58] Field of Search ........................ 544/363; 424/250

[56] References Cited

U.S. PATENT DOCUMENTS 4,146,719 3/1979 Irikura .................................. 544/363

OTHER PUBLICATIONS

Japanese Laid-Open Patent Publication No. 47658/1980.
J. Med. Chem. 1980, vol. 23, pp. 1358-1363.

Primary Examiner—Donald G. Daus
Assistant Examiner—James H. Turnipseed
Attorney, Agent, or Firm—Wenderoth, Lind & Ponack

[57] ABSTRACT

A novel quinolinecarboxylic acid derivative of the formula

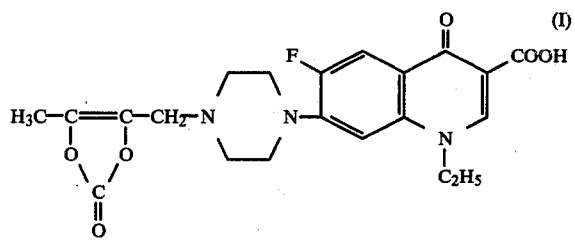

or a pharmaceutically acceptable salt thereof.

These compounds are useful as antibacterial agents, and are prepared by a process which comprises reacting a compound of the formula

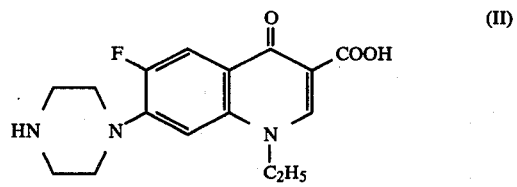

with a compound of the formula

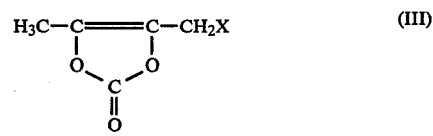

wherein X represents a halogen atom, and thereafter, as required, converting the resulting compound to a pharmaceutically acceptable salt thereof.

8 Claims, No Drawings

QUINOLINECARBOXYLIC ACID DERIVATIVE, AND ANTIBACTERIAL AGENT CONTAINING SAID COMPOUND AS ACTIVE INGREDIENT

This invention relates to a novel quinolinecarboxylic acid derivative, a process for the production thereof, and an antibacterial agent comprising the novel compound as an active ingredient.

Various synthetic antibacterial agents have been known, and nalidixic acid, piromidic acid and pipemidic acid are typical examples. These antibacterial agents exhibit good antibacterial activity against Gram-negative bacteria and are widely used as therapeutic agents for urinary tract infections. However, their effect against Gram-positive bacteria is not sufficient.

It was recently proposed to use 1-ethyl-6-fluoro-1,4-dihydro-4-oxo-7-piperazinylquinoline-3-carboxylic acid of the following formula

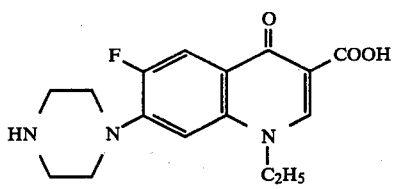

as an antibacterial agent (see U.S. Pat. No. 4,146,719). This compound is attracting attention because it exhibits excellent antibacterial activity against Gram-positive bacteria, against which conventional synthetic antibacterial agents have not proved to be satisfactorily effective, as well as Gram-negative bacteria and has a broad antibacterial spectrum. It has been found however that although the compound (II) exhibits very good antibacterial activity in vitro, it does not exhibit the expected efficacy when administered orally to animals and humans and thus has insufficient gastro-intestinal absorbability or bioavailability.

A method has heretofore been known to remedy this defect by converting a drug to a prodrug. According to this method, a drug having low absorbability from the intestinal tract, for example, is partially modified chemically with a suitable protective group (promoiety) to increase its intestinal absorption, and the modified drug is returned to the original drug by chemical and biological actions in vivo, wherein the inherent pharmacological activity of the drug is efficiently exhibited. On extensive investigations, we have now found that a novel derivative having a novel protective group and represented by the following formula (I), i.e. 1-ethyl-6-fluoro-1,4-dihyro-4-oxo-7-[4-(5-methyl-2-oxo-1,3-dioxolen-4-yl)-methyl-1-piperazinyl]quinoline-3-carboxylic acid, has satisfactory properties as a prodrug for the aforesaid known antibacterial agent of formula (II), and exhibits extremely low toxicity.

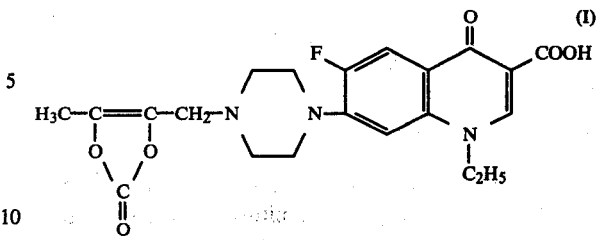

It is an object of this invention therefore to provide a novel quinolinecarboxylic acid derivative.

Another object of this invention is to provide a novel prodrug for the known antibacterial compound of formula (II).

Still another object of this invention is to provide a process for producing the aforesaid novel compound.

A further object of this invention is to provide an antibacterial agent useful for the treatment of various infections, which comprises the aforesaid novel compound as an active ingredient.

The above objects are achieved in accordance with this invention by a novel quinolinecarboxylic acid derivative of the formula

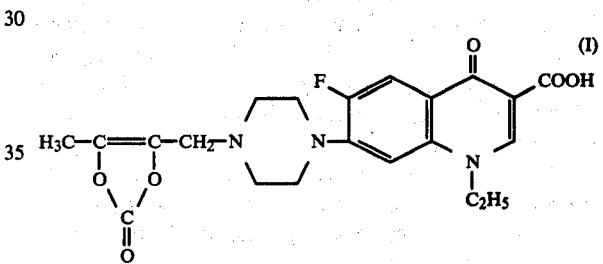

or a pharmaceutically acceptable salt thereof; a process for producing a novel quinolinecarboxylic acid derivative of the formula

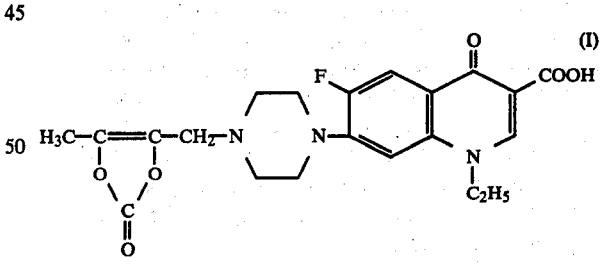

or a pharmaceutically acceptable salt thereof, which comprises reacting a compound of the formula

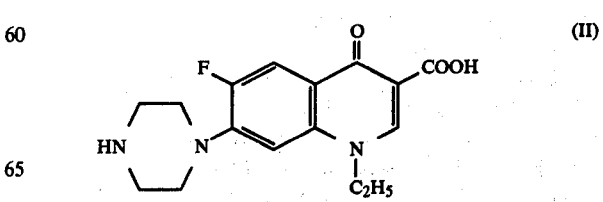

with a compound of the formula

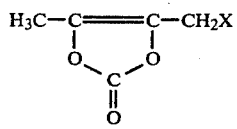

(III)

wherein X represents a halogen atom, and thereafter, as required, converting the resulting compound into a pharmaceutically acceptable salt; and an antibacterial agent comprising as an active ingredient a novel quinolinecarboxylic acid derivative of the formula

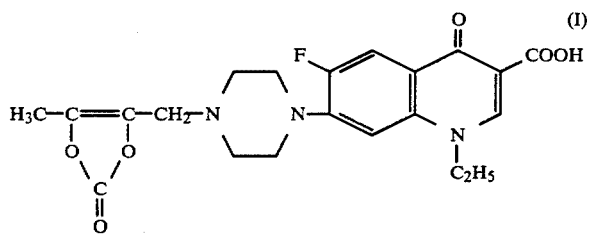

(I)

or a pharmaceutically acceptable salt thereof.

Examples of the pharmaceutically acceptable salts of the compound (I) of the invention include metal salts such as a sodium, potassium or calcium salt; organic base salts such as an ethanolamine salt; and acid addition salts, for example inorganic acid salts such as a hydrochloride or sulfate, and organic acid salts such as a p-toluenesulfonate or acetate. Of these, the acid addition salts are preferred.

The compound of formula (I) in accordance with this invention has various excellent properties as a prodrug for the known antibacterial compound of formula (II). The compound of this invention is invulnerable to non-enzymatic hydrolysis in the stomach and intestines (see Test Example 2 given hereinbelow), but is easily decomposed enzymatically in the blood to the compound of formula (II) (see Test Example 3 given hereinbelow). In an actual pharmacological test in vivo by oral administration, the compound (I) of this invention is absorbed and moves to the blood more rapidly than the compound of formula (II) and easily liberates the compound of formula (II) and provides a fully satisfactory level of the compound (II) in the blood (see Test Example 1 given hereinbelow). Moreover, the compound of this invention has extremely low toxicity (see Test Example 4 given hereinbelow).

On the other hand, in a minimum inhibitory concentration test in vitro, the compound of formula (I) of this invention is inferior to the compound of formula (II) both against a Gram-positive bacterium (*Bacillus subtilis* ATCC 6633) and a Gram-negative bacterium (*Escherichia coli* NIHJ JC-2).

Japanese Laid-Open Patent Publication No. 47658/1980 discloses various derivatives of the compound (II), among which is a derivative resulting from modification of the 4-position of the piperazine ring as in the present invention. However, a derivative (IV) in which the 4-position of the piperazine ring is substituted by a phthalidyl group, for example,

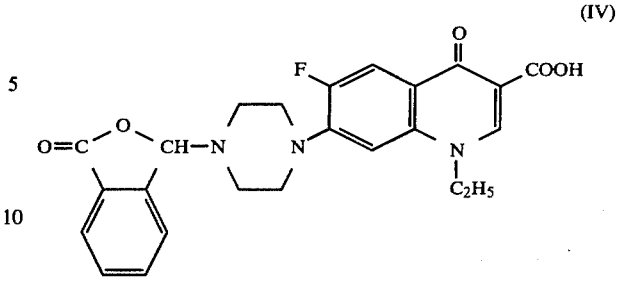

(IV)

has slightly superior antibacterial activity in vitro to the parent compound (II), but is less effective than the compound (II) in a test of oral administration to animals (see Test Example 1). It is anticipated therefore that the absorbability of bioavailability of the derivative (IV) in oral administration will be worse. In view of this fact, it is quite surprising that the compound of the invention which is also a derivative from modification of the 4-position of the piperazine ring of the compound (II) can be an effective antibacterial agent in oral administration.

Examples of the results of pharmacological tests are given below which show the efficacy of the compound of this invention.

TEST EXAMPLE 1

Antibacterial activity in oral administration to mice:
(1) Test compounds
(A) 1-Ethyl-6-fluoro-1,4-dihydro-4-oxo-7-[4-(5-methyl-2-oxo-1,3-dioxolen-4-yl)methyl-1-piperazinyl]quinoline-3-carboxylic acid (the compound (I) of the invention)
(B) 1-Ethyl-6-fluoro-1,4-dihydro-4-oxo-7-piperazinylquinoline-3-carboxylic acid [the compound (II) used as a control]
(C) 1-Ethyl-6-fluoro-1,4-dihydro-4-oxo-7-(4-phthalidyl-1-piperazinyl)quinoline-3-carboxylic acid [compound (IV) used as a control]
(2) Test method An amount, corresponding to 100 mg/kg calculated as compound II, of a suspension (concentration about 10%) of each of the test compounds in a 0.5% aqueous solution of carboxymethylcellulose was orally administered to male ddY-strain mice (body weight about 25 g; five per group) which had been fasted for 16 hours. After the administration, the blood was taken from the mice periodically to prepare serum. The sera obtained from five mice in each group for each blood sampling time were mixed in equal proportions.

The antibacterial activity (the diameter of an inhibitory circular zone, mm) of the mixed serum was determined by a bioassay method using *Bacillus subtilis* ATCC 6633 (Gram-positive bacterium) and *Escherichia coli* NIHJ JC-2 (Gram-negative bacterium) as test bacteria. The concentration ($\mu$g/ml) of the compound (II) for each of the diameters of the inhibitory zones in the above experiments was determined by using a separately prepared calibration curve showing the relation between the concentration ($\mu$g/ml) of the compound (II) and the diameter (mm) of the inhibitory zone.

(3) Results

Table 1 shows the results obtained when using *Bacillus subtilis* ATCC 6633, and Table 2, the results obtained when using *Escherichia coli* NIHJ JC-2.

TABLE 1

| Compound tested | Diameter of the inhibitory zone (mm) (the concentration of the compound (II) μg/ml) | | | |
|---|---|---|---|---|
| | Blood letting time (hours) | | | |
| | 0.5 | 1 | 2 | 4 |
| Compound (I) (invention) | 25.1 (10.2) | 24.1 (7.7) | 21.7 (4.5) | 16.4 (1.3) |
| Compound (II) (control) | 17.8 (1.8) | 17.5 (1.7) | 18.0 (1.9) | 13.5 (0.7) |
| Compound (IV) (control) | 16.5 (1.3) | 14.9 (0.9) | 14.5 (0.8) | 12.0 (0.5) |

TABLE 2

| Compound tested | Diameter of the inhibitory zone (mm) (the concentration of the compound (II) μg/ml) | | | |
|---|---|---|---|---|
| | Blood letting time (hours) | | | |
| | 0.5 | 1 | 2 | 4 |
| Compound (I) (invention) | 30.0 (9.8) | 29.1 (7.6) | 26.9 (4.5) | 22.1 (1.3) |
| Compound (II) (control) | 23.2 (1.7) | 23.0 (1.6) | 23.8 (2.0) | 19.4 (0.7) |
| Compound (IV) (control) | 22.7 (1.5) | 20.4 (0.9) | 20.4 (0.9) | 17.9 (0.5) |

TEST EXAMPLE 2

Stability in acidic and basic media

A. Stability in an acidic medium (corresponding to artificial gastric juice)

(1) Test method

A solution of 3 mg of the compound (I) of the invention in a tiny amount of dimethylformamide was added to 5 ml of an aqueous solution at a pH of 1.2 containing 2.0 g of sodium chloride and 24 ml of 10% hydrochloric acid per 1,000 ml of the solution. The mixture was shaken at 37° C. The resulting solution was periodically sampled, and the concentration of the compound (I) of the invention in the solution was measured by high-performance liquid chromatography. The ratio of the remaining compound (I) was calculated from the ratio of the measured concentration to the initial concentration. High-performance liquid chromatography was carried out by using a column of Microbondapak C-18 (a product of Waters Co.) using a 40:60 mixture of 0.1 M citrate buffer (pH 4.0) and methanol as a solvent.

(2) Results

TABLE 3

| Elapsed time (hours) | 1 | 2 | 3 | 4 | 5 | 6 |
|---|---|---|---|---|---|---|
| Ratio of the remainder (%) | 94 | 89 | 84 | 79 | 76 | 73 |

B. Stability in a basic medium (corresponding to artificial intestinal juice)

(1) Test method

The same procedure as in A above was taken except that an aqueous solution at a pH of 7.5 containing 35.8 g of disodium phosphate and 6.0 ml of 10% hydrochloric acid per 1000 ml of the aqueous solution was used as the medium.

(2) Results

TABLE 4

| Elapsed time (hours) | 1 | 2 | 3 | 4 | 5 | 6 |
|---|---|---|---|---|---|---|
| Ratio of the remainder (%) | 91 | 85 | 80 | 69 | 54 | 40 |

The above results show that the compound (I) of this invention has sufficient stability in the digestive tract in oral administration.

TEST EXAMPLE 3

Stability in the serum:

The compound (I) of the invention was dissolved to a concentration of about 3 mg/ml in a 0.1 M phosphate buffer (pH 7.4) containing 25% of horse serum, and its stability at 37° C. was examined by bioautography using *Bacillus subtilis* ATCC 6633 as a test bacterium.

It was found that the compound (I) rapidly decomposed (in about 15 minutes) and converted to the compound (II) in the above solution.

TEST EXAMPLE 4

Toxicity test:

The compound (I) of the invention was suspended in a 0.5% aqueous solution of carboxymethylcellulose, and the suspension was orally administered to male ddY-strain mice (body weight about 25 g, five per group), and its acute toxicity ($LD_{50}$) was measured. No death was noted even when the dose was 4,000 mg/kg. Accordingly, the $LD_{50}$ (oral) of the compound (I) of this invention can be determined to be more than 4,000 mg/kg. This value shows that the compound (I) of the invention has extremely low toxicity.

The compound (I) of this invention can be produced by reacting a compound of the formula

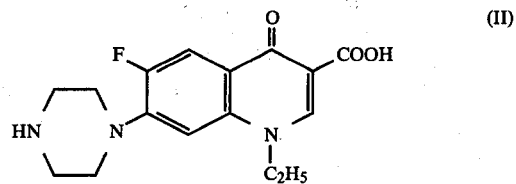

(II)

with a compound of the formula

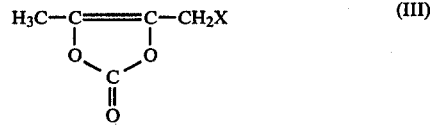

(III)

wherein X is as defined hereinabove.

The compound (II) is known from U.S. Pat. No. 4,146,719 and The Journal of Medicinal Chemistry, Vol. 23, page 1358 (1980). The compound (II) can be easily synthesized by reacting 1-ethyl-6-fluoro-7-chloro-4-oxo-1,4-dihydroquinoline-3-carboxylic acid of the following formula

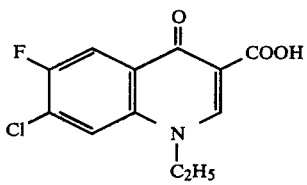

with an equimolar amount or a molar excess of piperazine in the absence of a solvent or in a polar solvent such as water, ethanol, dimethylformamide or hexamethylphosphoric triamide, preferably at a temperature of 100° to 180° C.

The compound (III) can be obtained by halogenating 4,5-dimethyl-2-oxo-1,3-dioxolene of the following formula:

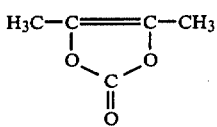

The starting compound of formula (V) is known, and disclosed, for example, in Transactions, Illinois State Academic Science, vol. 67, pages 139-144, (1974); Tetrahedron Letters, (1972), pages 1701-1704; and U.S. Pat. No. 3,020,290.

To produce a compound of formula (III) in which X is chlorine or bromine, the compound (V), may be reacted with at least one mole, per mole of the compound (V), of a chlorinating or brominating agent such as chlorine, bromine, N-bromophthalimide, N-bromosuccinimide, N-chlorophthalimide, and N-chlorosuccinimide in an inert organic solvent such as methylene chloride, chloroform, carbon tetrachloride or benzene, preferably under radical-initiating conditions. A compound of formula (III) in which X is iodine can be obtained by subjecting the resulting chlorinated compound [X is a chlorine atom in formula (III)], or the resulting brominated compound (X is a bromine atom in formula (III)] to a halogen-substitution reaction in a customary manner using potassium iodide, etc.

The reaction of forming the compound (I) of this invention from the compound of formula (II) and the compound of formula (III) obtained as above is carried out by the action of the compound (III), particularly the compound (III) in which X is chlorine or bromine, in an amount of preferably at least 1 mole per mole of the compound of formula (II), upon the compound (II) in the absence of a solvent or in an aprotic inert-organic solvent such as dimethylformamide, dimethyl sulfoxide, or diglyme, suitably in the presence of a base such as an alkali hydrogen carbonate or an alkali carbonate, preferably at a temperature of −20° to +80° C., especially preferably −5° C. to room temperature, for a period of, say, 2 to 20 hours. The desired compound can be separated and purified, for example, by distilling off the solvent from the reaction mixture and adding water to the residue or directly adding water to the reaction mixture when no solvent is used, thereafter extracting the mixture with a suitable organic solvent such as chloroform, and then recrystallizing the extract from a suitable solvent such as chloroform/ether.

The salt of the compound (I) of the invention can be easily produced in a customary manner by, for example, treating the compound (I) with a corresponding basic compound or acid.

The compound (I) of the invention or its pharmaceutically acceptable salt is administered to a human being preferably through an oral route either singly or, generally, in admixture with usual non-toxic pharmaceutically acceptable additives such as starch, lactose, magnesium stearate, crystalline cellulose, kaolin, calcium carbonate and talc. It is used in the form of tablets, granules, fine granules or powders, or as capsules obtained by filling such fine granules or powders properly into capsules. The dosage varies depending upon the age, body weight, condition, etc. of the patient, but generally, it is 1 to 50 mg/kg body weight/day. Preferably, the daily dosage is administered in two to four divided portions.

The following examples illustrate the present invention more specifically.

EXAMPLE 1

Synthesis of 1-ethyl-6-fluoro-1,4-dihydro-4-oxo-7-[4-(5-methyl-2-oxo-1,3-dioxolen-4-yl)methyl-1-piperazinyl]quinoline-3-carboxylic acid:

(1) Synthesis of 4-bromomethyl-5-methyl-1,3-dioxolen-2-one[the compound of formula (III) in which X is a bromine atom]:

3.42 g of 4,5-dimethyl-1,3-dioxolen-2-one (synthesized in accordance with Tetrahedron Letters, (1972), pages 1701-1704) was dissolved in 150 ml of carbon tetrachloride, and 5.34 g of N-bromosuccinimide and a catalytic amount of α,α'-azobisisobutyronitrile were added. The mixture was heated under reflux for 15 minutes. The reaction mixture was concentrated to half of its volume and the resulting insoluble matter was removed by filtration. Concentrating the filtrate gave a syrupy residue. The residue was distilled under reduced pressure to give a fraction boiling at 115° to 120° C./5 mm Hg which was 4.2 g (yield 73%) of the captioned compound.

Appearance: Colorless liquid

Elemental analysis (for $C_5H_5BrO_3$): Calculated (%): C 31.12; H 2.61; Br 41.40. Found (%): C 31.30; H 2.49; Br 41.31.

IR (neat) ν (cm$^{-1}$): near 1825 (carbonyl).

NMR (CCl$_4$, δ ppm): 2.10 (3H, —C$\underline{H}_3$, s), 4.10 (2H, —C$\underline{H}_2$Br, s).

(2) Synthesis of 1-ethyl-6-fluoro-1,4-dihydro-4-oxo-7-[4-(5-methyl-2-oxo-1,3-dioxolen-4-yl)methyl-1-piperazinyl]quinoline-3-carboxylic acid:

3.2 g of 1-ethyl-6-fluoro-1,4-dihydro-4-oxo-7-piperazinylquinoline-3-carboxylic acid [the compound of formula (II) synthesized in accordance with The Journal of Medicinal Chemistry, vol. 23, page 1358 to 1363 (1980)], 2.3 g of 4-bromomethyl-5-methyl-1,3-dioxolen-2-one and 1.2 g of potassium hydrogen carbonate were suspended in 50 ml of dimethylformamide, and reacted for 5 hours under ice cooling. The solvent was distilled off from the reaction mixture under reduced pressure, and water was added to the residue. The mixture was extracted with chloroform. The extract was washed with water and dried. The chloroform was distilled off, and the residue was recrystallized from chloroform-ether to give 2.8 g (yield 66%) of a compound having the following properties.

Appearance: Pale yellow amorphous solid

Melting point: 184°-190° C. (decomp.).

Elemental analysis (for $C_{21}H_{22}O_6N_3F$):

Calculated (%): C 58.46; H 5.14; N 9.74; F 4.40
Found (%): C 58.20; H 5.14; N 9.73; F 4.39 IR (KBr) $\nu$ (cm$^{-1}$): 1810, 1725 (carbonyl).

NMR (DMSO-d$_6$, δ ppm):

1.43 (3H, —NCH$_2$CH$_3$, t), 2.15

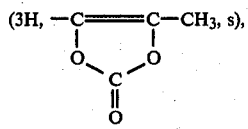

2.70 (4H, protons on piperazine ring, m), 3.35 (4H, protons on piperazine ring, m), 3.50

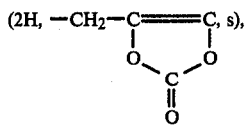

4.60 (2H, —NCH$_2$CH$_3$, q), 7.20 (1H, proton at 8-position, d), 7.90 (1H, proton at 5-position, d), 8.92 (1H, proton at 2-position, s), 15.3 (1H, COOH, s).

From the above data, the resulting compound was identified as the captioned compound.

EXAMPLE 2

Synthesis of 1-ethyl-6-fluoro-1,4-dihydro-4-oxo-7-[4-(5-methyl-2-oxo-1,3-dioxolen-4-yl)methyl-1-piperazinyl]quinoline-3-carboxylic acid hydrochloride:

2.15 g (5 mmol) of 1-ethyl-6-fluoro-1,4-dihydro-4-oxo-7-[4-(5-methyl-2-oxo-1,3-dioxolen-4-yl)methyl-1-piperazinyl]quinoline-3-carboxylic acid obtained in the same way as in Example 1 was dissolved in 400 ml of chloroform, and under ice cooling, 20 ml of 1 N HCl/methanol was gradually added dropwise. The mixture was stirred at room temperature for 30 minutes. The resulting solid was collected by filtration, recrystallized from methanol, and dried over P$_2$O$_5$ at 100° C. for 6 hours under reduced pressure to give 2.15 g (yield 92%) of a compound having the following properties as a white amorphous solid.

Melting point: 220°–225° C. (decomp.).

IR (KBr) $\nu$ (cm$^{-1}$): 2700–2250

1830, 1730 (carbonyl),

NMR (DMSO-d$_6$, δ ppm): 1.44 (3H, —NCH$_2$CH$_3$, t), 2.27

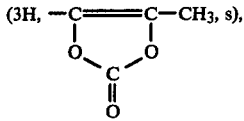

3.0–4.2 (8H, protons on piperazine ring, m), 4.43

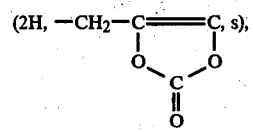

4.63 (2H, —NCH$_2$CH$_3$, q), 7.25 (1H, proton at 8-position, d), 7.91 (1H, proton at 5-position, d), 8.90 (1H, proton at 2-position, s).

Elemental analysis (for $C_{21}H_{22}O_6N_3F \cdot 2HCl$): Calculated (%): C 50.01; H 4.80; N 8.33; Cl 14.06. Found (%): C 50.46; H 4.82; N 8.47; Cl 13.62.

From the above data, the resulting solid was identified as the captioned compound.

EXAMPLE 3

Synthesis of 1-ethyl-6-fluoro-1,4-dihydro-4-oxo-7-[4-(5-methyl-2-oxo-1,3-dioxolen-4-yl)methyl-1-piperazinyl]quinoline-3-carboxylic acid p-toluenesulfonate 1.72 g (4 mmol) of the same carboxylic acid as obtained in Example 1 was dissolved in 250 ml of chloroform, and with stirring at room temperature, 100 ml of a chloroform solution containing 800 mg (4.2 mmol) of p-toluenesulfonic acid was gradually added dropwise. After the addition, the mixture was further stirred at room temperature for 30 minutes. The salt precipitated was collected by filtration, and washed with chloroform and then with diethyl ether. The solid was recrystallized from a mixture of chloroform and methanol, and then dried over P$_2$O$_5$ at 100° C. for 3 hours under reduced pressure to give 2.1 g (yield 84%) of a white amorphous solid having the following properties.

Melting point: 178°–183° C. (183°–190° C., decomp.).

Elemental analysis (for $C_{21}H_{22}O_6N_3F \cdot CH_3C_6H_4SO_3H \cdot H_2O$): Calculated (%): C 54.10; H 5.20; N 6.76; S 5.16 Found (%): C 54.29; H 4.92; N 7.04; S 5.03.

IR (KBr) $\nu$ (cm$^{-1}$): 2700–2300

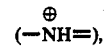

1815, 1710 (carbonyl).

NMR (DMSO-d$_6$, δ ppm): 1.45 (3H, —NCH$_2$CH$_3$, t),

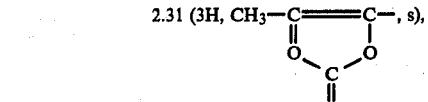

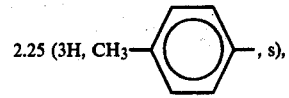

3.30–4.0 (8H, protons on piperazine ring, m), 4.49

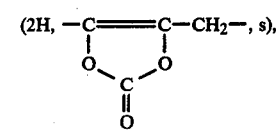

4.63 (2H, —NCH₂CH₃, q), 7.11 (2H, protons on benzene ring, d), 7.50 (2H, protons on benzene ring, d), 7.26 (1H, proton at 8-position, d), 7.94 (1H, proton at 5-position, d), 8.92 (1H, proton at 2-position, s).

From the above data, the resulting compound was identified as the captioned compound.

EXAMPLE 4

Tablets:

| Recipe | |
| --- | --- |
| Active ingredient (*1) | 40.0 g |
| Lactose | 12.0 g |
| Corn starch | 8.0 g |
| Crystalline cellulose | 8.6 g |
| Hydroxypropylcellulose | 0.8 g |
| Magnesium stearate | 0.6 g |
| | 70.0 g |

(*1): 1-Ethyl-6-fluoro-1,4-dihydro-4-oxo-7-[4-(5-methyl-2-oxo-1,3-dioxolen-4-yl)methyl-1-piperazinyl]quinoline-3-carboxylic acid Procedure The active ingredient, lactose, corn starch and crystalline cellulose were mixed, and hydroxypropylcellulose dissolved in 16 ml of water was added. The mixture was fully kneaded. The kneaded mixture was granulated through a 20-mesh screen and dried. The resulting granules were mixed with magnesium stearate, and the mixture was tabulated into tablets each weighing 350 mg.

EXAMPLE 5

Capsules:

| Recipe | |
| --- | --- |
| Active ingredient (same as in Example 4) | 40.0 g |
| Lactose | 8.0 g |
| Corn starch | 6.0 g |
| Crystalline cellulose | 5.4 g |
| Magnesium stearate | 0.6 g |
| | 60.0 g |

Procedure

The above ingredients were fully mixed, and 300 mg of the mixture was filled in each of No. 2 capsules.

EXAMPLE 6

Granules:

| Recipe | |
| --- | --- |
| Active ingredient (same as in Example 4) | 40 g |
| Lactose | 40 g |
| Corn starch | 19 g |
| Hydroxypropylcellulose | 1 g |
| | 100 g |

Procedure

The active ingredient, lactose and corn starch were mixed and hydroxypropylcellulose dissolved in 20 ml of water was added. They were fully kneaded. The kneaded mixture was passed through a 20-mesh screen. The granules obtained were dried and adjusted in size to form granules.

What we claim is:

1. A compound of the formula

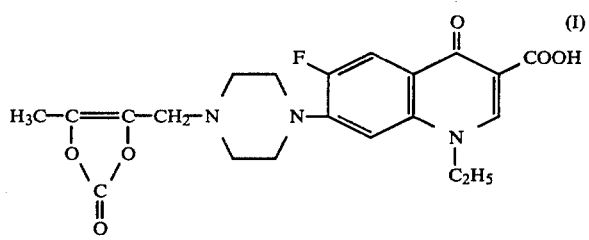

or a pharmaceutically acceptable salt thereof.

2. A salt according to claim 1, which is an acid addition salt.

3. A salt according to claim 2, which is a hydrochloride, sulfate, p-toluenesulfonate or acetate.

4. An antibacterial composition comprising as an active ingredient an antibacterially effective amount of a compound of the formula

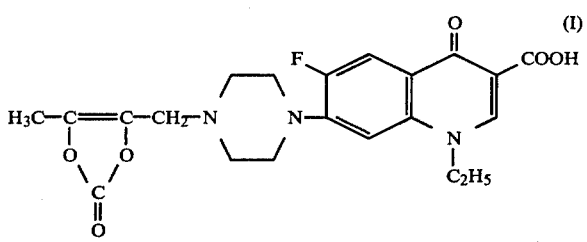

or a pharmaceutically acceptable salt thereof and a pharmaceutically acceptable carrier therefor.

5. An antibacterial composition according to claim 4 wherein the pharmaceutically acceptable salt is an acid addition salt.

6. An antibacterial composition according to claim 5 wherein the acid addition salt is a hydrochloride, sulfate, p-toluenesulfonate or acetate.

7. An antibacterial composition according to claim 4 which is in a unit dosage form for oral administration.

8. An antibacterial composition according to claim 7 which is in the form of tablets, granules, fine granules or capsules.

* * * * *